US012697126B1

(12) United States Patent
Gitlin

(10) Patent No.: US 12,697,126 B1
(45) Date of Patent: Aug. 4, 2026

(54) TAMPONADE DEVICE

(71) Applicant: David Gitlin, Naples, FL (US)

(72) Inventor: David Gitlin, Naples, FL (US)

(73) Assignee: Gitlin LLC, Naples, FL (US)

( * ) Notice: Subject to any disclaimer, the term of this patent is extended or adjusted under 35 U.S.C. 154(b) by 25 days.

(21) Appl. No.: 18/973,451

(22) Filed: Dec. 9, 2024

Related U.S. Application Data

(60) Provisional application No. 63/612,138, filed on Dec. 19, 2023.

(51) Int. Cl.
*A61B 17/12* (2006.01)
*A61B 17/00* (2006.01)

(52) U.S. Cl.
CPC .... *A61B 17/12136* (2013.01); *A61B 17/1204* (2013.01); *A61B 17/12099* (2013.01); *A61B 2017/00557* (2013.01); *A61B 2017/00566* (2013.01); *A61B 2017/00862* (2013.01); *A61B 2017/12004* (2013.01)

(58) Field of Classification Search
CPC ........ A61B 17/12022; A61B 17/12172; A61B 2017/00557; A61B 17/42; A61B 17/12136; A61B 17/1219; A61B 2217/005; A61M 25/1002; A61M 29/02; A61M 25/10; A61M 2025/1086; A61M 2025/006; A61M 2025/1004; A61M 2025/1031; A61M 2025/1081; A61M 2025/109; A61M 2025/1088; A61M 2039/2406
See application file for complete search history.

(56) References Cited

U.S. PATENT DOCUMENTS

| | | | |
|---|---|---|---|
| 4,552,557 A | 11/1985 | Rangaswamy | |
| 5,649,902 A * | 7/1997 | Yoon .................. | A61B 17/3421 604/11 |
| 6,306,154 B1 | 10/2001 | Hudson et al. | |
| 8,828,050 B2 | 9/2014 | Gregory et al. | |
| 10,918,838 B2 | 2/2021 | Ramsey, III | |
| 11,291,473 B2 | 4/2022 | Norred et al. | |
| 2014/0309687 A1 | 10/2014 | Atkinson et al. | |
| 2015/0133772 A1* | 5/2015 | Miesse .................. | A61M 25/04 604/8 |

* cited by examiner

*Primary Examiner* — Mohamed G Gabr

(57) ABSTRACT

In embodiments of the invention, an inflatable elastic-balloon-type tamponade device provides improved control of bleeding within a wound or other cavity by virtue of a suction element, disposed on the outside of the device, to which suction is applied after insertion of the tamponade device into the wound or other cavity. Embodiments of the invention may further include cladding elements disposed on the outside surface of the balloon in such a way that when the tamponade device is in its uninflated state, the cladding elements form a kind of housing that facilitates insertion of the tamponade device into the wound or other cavity and that encases the balloon and other elements that may be disposed on or in the balloon so as protect them from damage, during insertion, from sharp foreign objects that may be in the wound or cavity.

11 Claims, 2 Drawing Sheets

*FIG. 1*
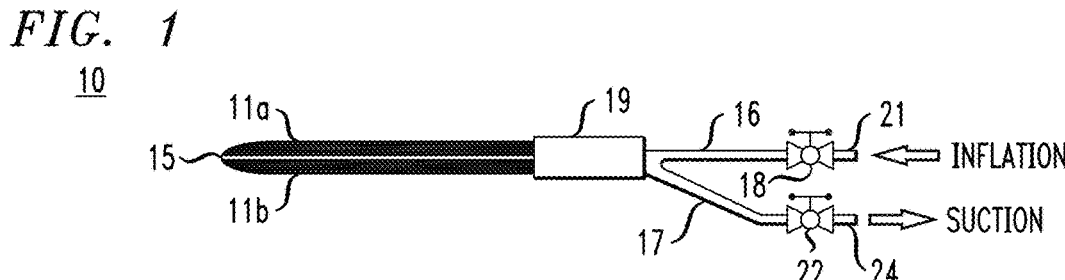
*FIG. 2*
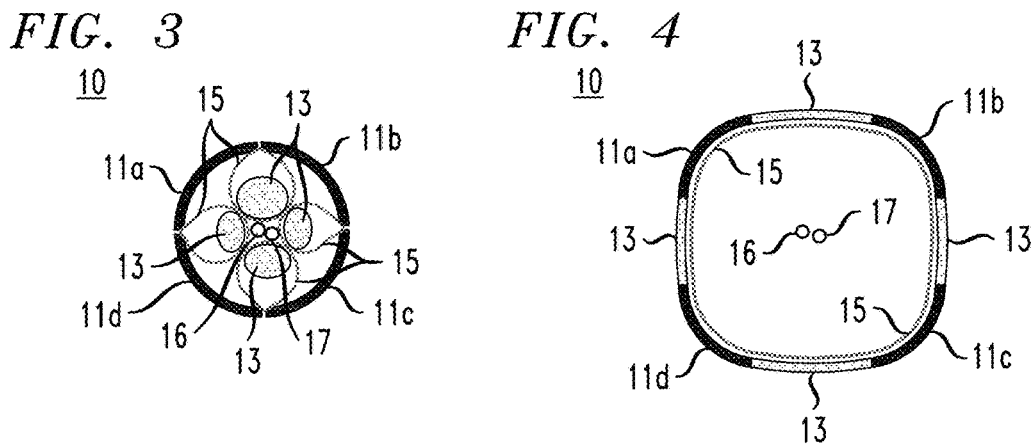
*FIG. 3*
*FIG. 4*
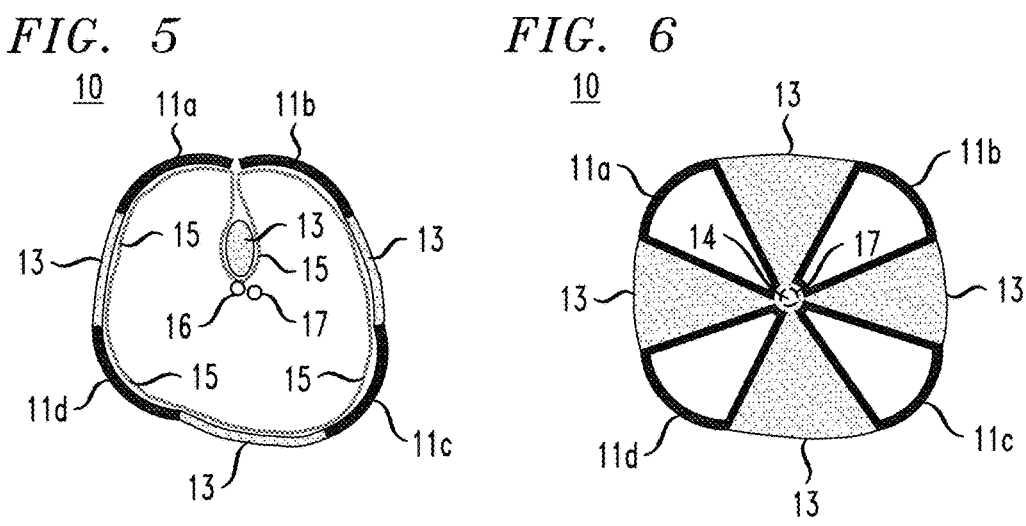
*FIG. 5*
*FIG. 6*

TAMPONADE DEVICE

CROSS-REFERENCE TO RELATED APPLICATION

This application claims the benefit of provisional patent application 63/612,138 received Dec. 19, 2023.

FIELD OF THE INVENTION

The present invention relates to the field of medical devices and, in particular, medical devices that may be used, for example, in surgery and emergency medicine.

BACKGROUND OF THE INVENTION

Bleeding-related deaths account for approximately 50% of combat-related deaths due to uncontrolled bleeding. These bleedings are generally non-compressible and occur mostly from penetrating injuries of the torso. However significant penetrating injuries to the extremities can also lead to non-compressible and uncontrollable bleeding. The most successful treatment of extremity vascular injury has been the tourniquet which can be applied proximal to a bleeding injury. Tourniquets were used effectively in combat and redesigned many times since their widespread use in World War II.

However, areas on the torso and in junctional areas, meaning the inguinal area and the axillary region, where the extremities meet the torso, do not allow the use of tourniquets. For injuries in the junctional areas there are a number of devices on the market that create an external tamponade (pressure) to provide a direct compression to an artery or vein. Among the devices disclosed in prior art are clamps to be applied externally to the skin that may prevent blood from escaping the body, such as disclosed in U.S. patent publication 2014/0309687 A1. Another alternative is an expandable foam product that is to be directly delivered into a cavity to create an internal tamponade, such as disclosed in U.S. Pat. No. 8,828,050.

Yet another approach for controlling penetrating-injury bleeding is the inflatable balloon-type tamponade device. One such device, disclosed in U.S. Pat. No. 10,918,838, comprises a non-elastic balloon that unrolls to fit the size of the cavity in which it has been inserted. It is made of a non-elastic material to prevent tearing of the balloon because many penetrating wounds incurred in combat contain sharp objects such as bone fragments or shrapnel, and a non-elastic material can be more resistant to tears or other damage than an elastic material. On the other hand, an elastic balloon has the benefit of being more readily able conform to the shape of whatever wound or other cavity the tamponade device has been inserted into. Indeed, U.S. Pat. No. 6,306,154, among many others, discloses an elastic-balloon-type tamponade device. That particular device comprises an elastic tamponade balloon with a hemostatic shroud that can be removed with the balloon or can be left behind for later removal for continued hemostasis.

Tamponade devices for use in non-combat settings are also known. For example, the so-called Bakri balloon tamponade device, designed specifically for the treatment of uterine bleed, comprises an expandable balloon that is placed into the uterus to provide temporary internal tamponade. Indeed, there are many variations of these uterine balloon-type tamponade devices. One of them, in particular, as disclosed in U.S. Pat. No. 4,552,557, is a tamponade device comprising an inflatable balloon with some suction elements around it's proximal end for the suction and removal of fluids.

Also it is known that suction can be used to control bleeding. The way this may be done is through suction of tissues adjacent to the bleeding area to thereby allow control of the bleed indirectly. U.S. Pat. No. 11,291,473 discloses one example of this technique.

SUMMARY OF THE INVENTION

The present invention is directed to solving various problems that are manifest in elastic-balloon-type tamponade devices-problems that I have recognized can be ameliorated. One problem, I have recognized, is that while the prior art elastic-balloon-type tamponade devices can achieve at least some degree of bleeding control, further improvement in that realm is possible. The inflated balloon should, of course, conform to the shape of the wound cavity as much as possible for best tamponade. However, even after the device has been inflated, there may be poor or no contact between the tamponade device and areas of the internal wall of the wound or other cavity, depending on the particular characteristics of the device, the shape of the cavity, etc., with the result that bleeding at those areas may not be effectively controlled.

Another problem is that because the elastic-type balloon is quite flexible, insertion of prior art elastic-balloon-type tamponade devices into a wound or other cavity may not be particularly straightforward. For example, a (rigid) trocar or other ancillary device might be required for effective insertion. Alternatively, an elastic-balloon-type tamponade device might be manually pushed little-by-little into the wound or other cavity, but this may lead to less-than-ideal placement and/or less-than-ideal conformation of the device once inserted and inflated.

Yet another problem that can be solved, I have realized, is one mentioned above-namely that bone fragments, shrapnel, or other sharp objects that may be within the wound or other cavity may well tear or otherwise damage an elastic balloon upon insertion.

The foregoing problems are addressed in accordance with the principles of the present invention.

In embodiments of the invention, improved control of bleeding within a wound or other cavity is achieved by applying negative pressure, or suction, to a suction element disposed on the outside of the distal end of an elastic-balloon-type tamponade device once the device has been inserted into a cavity. Among several advantageous effects of this is that internal walls of the cavity are drawn closer, and/or more tightly, to the surface of the tamponade device than would otherwise be the case, i.e., that would be the case without the suction element and the suction applied thereto. The suction element may be, for example, a piece of open-cell foam shaped and positioned on the surface of the balloon so as to extend to multiple areas on the balloon surface. The suction may be applied via conduit, illustratively a length of tubing or the like, connected to the suction element either during or after balloon inflation, the tubing or other suction-delivery device extending from outside the tamponade device through the inside of the balloon to a distal end of the balloon and connected at the distal end to a central region of the suction element.

In embodiments of the invention, an elastic-balloon-type tamponade device includes elements that serve at least one of two additional functions. One function is to shield at least a portion of the balloon from possible damage as the tamponade device is inserted into a wound or other cavity—notably damage from sharp objects that may be inside the cavity, such as bone fragments and shrapnel. Another function is to make the overall tamponade device sufficiently rigid as to facilitate easy insertion of the tamponade device into a wound or other cavity without the need for a trocar or other auxiliary component. In particular ones of these embodiments, both functions are provided by cladding elements that are at least more rigid than the balloon itself- and are, illustratively, rigid or semi-rigid, The cladding elements are disposed on the outside surface of the balloon in such a way that when the tamponade device is in its uninflated state, the cladding elements form a kind of housing that encases and thus protects the balloon and other elements that may be disposed on or in the balloon, such as the aforementioned suction element in embodiments that include the suction element as well as the cladding elements.

Further embodiments of the invention include both a) the cladding elements, and b) the suction element and associated component(s) for attachment to a suction source.

BRIEF DESCRIPTION OF THE DRAWING

FIG. 1 is a side view of an elastic-balloon-type tamponade device embodying the principles of the invention in its initial, non-inflated state;

FIG. 2 is a side view of the tamponade device of FIG. 1 in its inflated state;

FIG. 3 is a cross-sectional front, i.e. distal end, view of the tamponade device of FIG. 1 in its initial, non-inflated state;

FIG. 4 is a cross-sectional front, i.e. distal end, view of the tamponade device of FIG. 1 in its inflated state;

FIG. 5 is a cross-sectional view of the tamponade device of FIG. 1 in its inflated state wherein a part of the balloon has failed to deploy;

FIG. 6 is a front, i.e., distal end, view of the tamponade device of FIG. 1 in its inflated state;

DETAILED DESCRIPTION OF EMBODIMENTS OF THE INVENTION

FIGS. 1-6 show various views of an elastic-balloon-type tamponade device 10 embodying the principles of the invention.

The tamponade device comprises a flexible or semi-flexible balloon 15 at which or on which are four less flexible, rigid or semi-rigid cladding elements 11a-11d. Attached to the balloon 15 in the areas between the cladding elements are the arms of a porous suction element 13 which meet at a central region of the suction element on the surface of the distal (in the FIGS., the left side) end 14 of balloon 15 as can be particularly well seen in FIG. 6. Suction element 13 thus has the general shape of a plus-sign in this particular embodiment, with the arms being disposed between respective pairs of cladding elements 11a-11d. Both the cladding elements 11a-11d and the arms of the suction element 13 extend from the distal end of the balloon 15 toward the proximal end along the balloon surface. Suction element 13 is illustratively comprised of open-cell foam or some other porous material. Suction element 13 is tacked or otherwise adhered to the balloon, such as with a compatible adhesive material at, illustratively, only the distal end 14 of the balloon so that the balloon will not be restricted from fully expanding, which might otherwise be the case if suction element 13 were to be adhered to the balloon at multiple places along the balloon surface. That being said, it might also be possible to adhere suction element 13 to the balloon at its proximal end (in the FIGS., its right side) as long as enough "slack" is left in the suction element so as to allow balloon 15 to freely expand.

The tamponade device is initially in the uninflated state shown in FIGS. 1 and 3, wherein balloon 15 and its attached suction element 13 are contained within what is effectively a housing comprising the cladding elements 11a-11d. As can be seen in FIG. 3, the cladding elements taper at their ends and their respective ends come close to one another at balloon distal end 14. As a result, when the tamponade device is in its uninflated state the cladding elements form a kind of housing that encases and thus protects the more damage-prone components-balloon 15 and suction element 13—from being torn or otherwise damaged during insertion of the tamponade device into a wound or other cavity (hereinafter "cavity") that may contain bone fragments, shrapnel or other sharp foreign objects.

In addition, cladding elements 11a-11d create a smooth and rigid or semi-rigid surface for the tamponade device in its uninflated state, thereby giving the device a rigid or semi-rigid form when placed into a cavity, obviating the need for a trocar or other rigid or semi-rigid device to be able to easily guide the tamponade device into a cavity.

Figure 7:
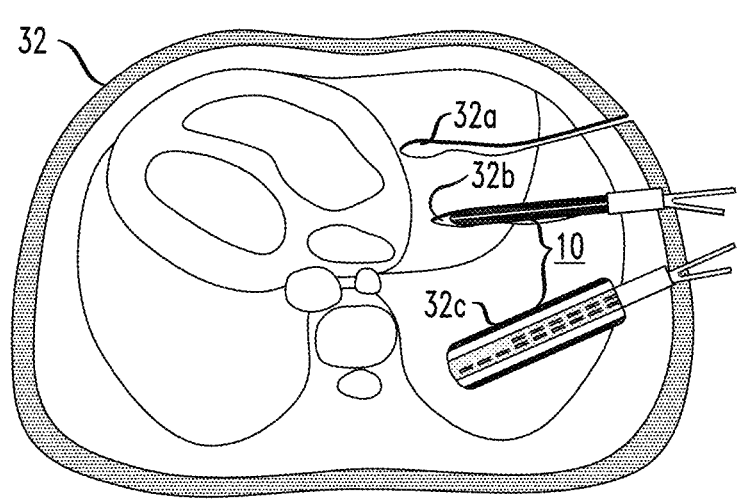
FIG. 7 is a cross-sectional view of a torso with penetrating wounds showing the tamponade device of FIG. 1 in its non-inflated and inflated states in respective ones of the wounds.

FIG. 7 shows a cross-section of a torso 32 with three penetrating wounds 32a, 32b and 32c, with not-as-yet inflated tamponade device 10 having been inserted into wound 32b.

Returning now to the previously referenced FIGS., it can be seen that tamponade device 10 further includes hollow cylindrical end piece 19 onto which balloon 15 is fused. Extending through end piece 19 and thence into the interior of balloon 15 is tubing 16. Once the tamponade device has been inserted into a cavity, an inflating medium, which can be a gas, such as air or nitrogen, or a liquid will be pumped into the balloon from a gas or liquid reservoir (not shown) via tubing 21 and, if desired, at least a first valve 18—then in the open position as shown in FIG. 1—and tubing 16. A Luer lock connector or other known device (not shown) can be used to attach the gas or liquid reservoir to tubing 21. After inflation, valve 18 can be turned to its closed position, as shown in FIG. 2, thereby trapping the inflation gas or liquid inside the tamponade device so that the gas or liquid reservoir can thereafter be removed from tubing 21 whilst the inflating medium remains within the device.

The introduction of the gas or liquid into balloon 15 once the tamponade device has been inserted into a cavity causes the tamponade device to expand and to thus exert pressure against the interior walls of the cavity to thereby control the bleeding that is occurring. This is shown in FIG. 7 wherein the tamponade device 10 inserted into cavity 32c has been inflated so as to push against the interior walls of wound 32c. The role of cladding elements 11a-11d and suction element 13 in achieving this is described in detail hereinbelow.

The thus inflated device is depicted for simplicity in the FIGS. as having a particular cross-sectional shape, such as a quadrilateral shape with rounded corners as shown in FIG. 4. Indeed, tamponade device 10 would take on that general type of shape if it were inflated outside of a cavity. However when inflated within a cavity, the device will push against the tissues forming interior walls of the cavity and will take on a shape dictated in large part by the shape of the cavity. Thus although tamponade device 10 within wound 32*c* is shown for simplicity in FIG. 7 as having a generally rectilinear shape, the tamponade device will, as just noted, take on a shape dictated in large part by the shape of wound 32*c*.

It is also to be noted that, as depicted in FIG. 5, some portion or portions of the balloon may not fully expand due to, for example, possible damage to the balloon at a particular location or, for example, as a consequence of the shape of the cavity, but in such cases the tamponade device will still function as desired.

As the tamponade device expands in response to the introduction of the inflating medium, significant portions of the cladding elements 11*a*-11*d* and/or of suction element 13 will contact, and thus apply pressure to, the adjacent walls of the cavity. If this was all that was done, however, there might remain gaps between the tamponade device and portions of the walls of the cavity. This is disadvantageous inasmuch as bleeding may be occurring there and without the pressure of the tamponade device pressing against those portions of the walls, uncontrolled bleeding may persist there. The aforementioned gaps may be the result of, for example, pockets of trapped, and now compressed, air preventing the tamponade device from expanding to reach certain portions of the cavity walls and, as well, may also be the result of the specific geometries of the tamponade device and the cavity.

In accordance with a feature of the invention, however, such gaps can be eliminated or at least substantially reduced. In particular, tamponade device 10 further includes a suction portal in the form of tubing 17 adapted to be attached to a suction machine or other suction device (not shown). Unlike tubing 16, whose distal end terminates within balloon 15, tubing 17 extends fully through balloon 15 and its distal end is affixed to, or is embedded in, suction device 13. The distal end of tubing 17 extending through balloon 15 and terminating on the center portion of suction element 13 is represented with dashed lines in FIG. 6 so as to indicate that that distal end of tubing 17 is attached to the underside of suction element 13 or is embedded therewithin.

Suction applied to the proximal end of tubing 17 by the aforementioned suction machine or other suction device (not shown) via tubing 24 and, if desired, at least one valve 22—then in the open position as shown in FIG. 1—pervades suction element 13 whereupon suction element 13 exerts an inward-pulling negative pressure on the cavity walls. Sections of the cavity walls that to that point had not been in contact with the tamponade device due to gaps between the tamponade device and the cavity walls, as aforementioned, will thereupon be pulled toward, and onto, suction element 13 and possibly also cladding elements 11*a*-11*d* to control bleeding at those locations. In addition, cavity walls that were already in contact with the tamponade device—and in particular suction element 13—prior to the initiation of suction either during or after inflation will thereby be held more tightly against the tamponade device than would otherwise be the case, potentially enhancing the control of bleeding at those locations. The suction will also serve to pull blood or other liquids through the suction device into tubing 17 and thus out of the cavity. If desired, valve 22 can thereupon be closed, as shown in FIG. 2, and the suction machine or other suction device removed whilst the aforementioned negative pressure is maintained.

A number of factors can be at play at this time to provide enhanced bleed control. One of these, as already noted, is that suction pervading suction element 13 can help pull the walls of the cavity toward the tamponade balloon and to thus provide, or improve, pressure of the tamponade device against the cavity wall. In addition, when the suction element engages with the cavity wall at various locations, it can subdivide the cavity and create smaller artificial cavities whereby blood can be prevented from pooling in areas away from the bleeding tissues.

Tubing 17 can also be used to deliver antibiotics, coagulants or any other medications into the cavity.

Figure 8:
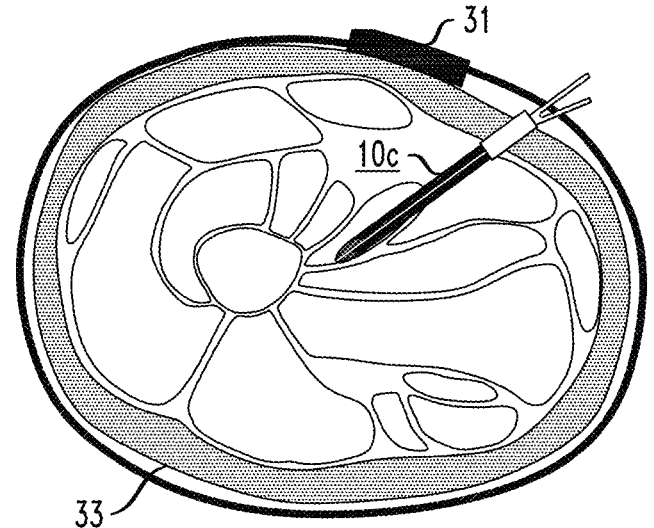
FIG. 8 is a cross-sectional view of a leg with a penetrating wound into which the tamponade device of FIG. 1, still in its non-inflated state, has been inserted and further shows a tourniquet or bandage placed around the leg.

As depicted in FIG. 8, a tourniquet 31 can be attached to the tamponade device when it is in place in a wound, say, in a leg. This will help to control bleeding as an adjunct to the tamponade device itself. The tourniquet can have a small hole (not shown) through which the proximal end of the tamponade device, e.g. tubings 16 and 17 and/or end piece 19, can be inserted to help keep the tamponade device in position once inserted in the cavity. Even if tourniquetting is not needed, a loose bandage or other band having such a hole can be put in place to help hold the tamponade device in position in situations where a tourniquet cannot be used, such as in the case of a torso wound.

Patents and other documents cited herein are hereby incorporated by reference in their entirety.

The foregoing merely illustrates the principles of the invention and those skilled in the art will be able to readily device further embodiments embodying those principles.

As one significant example, a tamponade device embodying the principles of the invention may include the cladding elements without the suction element if the only concern is ease of insertion and/or protection of the balloon during insertion. Alternatively, a tamponade device embodying the principles of the invention may include the suction element without the cladding elements if the aforementioned concerns vis-à-vis insertion are not an issue in a given situation.

The balloon portion of the overall tamponade device can be fabricated with a range of possible lengths and diameters for insertion into varying sizes of cavities. In particular embodiments, the length may be anywhere within the approximate range of 5 mm to 35 cm and the diameter anywhere within the approximate range of 5 mm to 100 cm. Embodiments wherein the tamponade device is particularly small are potentially useful for, for example, vascular surgical applications.

The various components of the tamponade device can be made from whatever materials might be appropriate depending, for example, on the intended application and the desired size. For example, balloon 15 can be silicone rubber or other elastic material; suction element 13 can be made of open-cell foam; cladding elements 11*a*-11*d* and end piece 19 can be plastic; tubings 16 and 17 can be of any material used for medical grade tubing.

Although the disclosed embodiment has four cladding elements and a four-arm suction element, any number of cladding elements and/or suction elements or suction element arms may be used, as may be deemed desirable for a given embodiment. Moreover, there need not be the same number of cladding elements as suction element arms. In addition, the cladding elements and the suction element(s) can have different shapes than those are shown herein.

Instead of open-cell foam or the like, the function of the suction element as described herein might be able to be carried out using, for example, perforated tubing rather than an open-cell foam or other permeable material.

Instead of having a continuous balloon onto which the cladding and/or suction element are attached, as in the disclosed embodiment, it may be possible to construct the tamponade device to have individual segments of elastic material that are connected between the ends of adjacent cladding elements, in which case the tampondae device's balloon would comprise alternating sections of elastic material and cladding elements, in which case the cladding elements would be at, rather than on, the surface of the balloon.

In order to effectuate the function of the cladding elements as described herein, it may be possible, instead of having separate cladding elements as disclosed herein, to manufacture a balloon having thickened and/or strengthened segments at the locations where the cladding elements would be.

The invention can be used in non-medical settings in which it may be desired to control, reduce or inhibit the flow of fluids or gasses in enclosed spaces.

It will thus be appreciated that those skilled in the art may be able to devise numerous alternative arrangements that, while not explicitly disclosed or suggested herein, embody the principles of the invention and thus are within their spirit and scope.

The invention claimed is:

1. An elastic-balloon-type tamponade device for controlling bleeding in a cavity, the tamponade device comprising
an inflatable, at least partially elastic, balloon having a distal end and a proximal end,
an inflation portal for applying an inflation medium to the interior of the balloon to inflate the balloon,
a suction element disposed on the outside surface of the balloon, and
a suction portal connected to the suction element,
wherein the suction element is configured in such a way that suction applied to the suction element via the suction portal when the tamponade device has been inserted into the cavity is distributed throughout portions of the suction element and thereupon into the cavity, whereby internal walls of the cavity are drawn closer, and/or more tightly, to the surface of the tamponade device than would otherwise be the case,
and wherein the suction portal comprises a suction conduit extending through the interior of the balloon and through a distal end of the balloon and terminating on or within the suction element, at least a portion of the suction element being disposed on the distal end of the balloon.

2. The elastic-balloon-type tamponade device of claim 1 wherein the suction element is comprised of a porous foam.

3. The elastic-balloon-type tamponade device of claim 1 wherein the suction element is comprised of a central region and one or more arms extending out from the central region along the surface of the balloon.

4. The elastic-balloon-type tamponade device of claim 3 wherein the suction element's central region is disposed on the distal end of the balloon.

5. The elastic-balloon-type tamponade device of claim 4 wherein the one or more arms of the suction element extend out along the surface of the balloon from the central region of the suction element from the distal end of the balloon toward the proximal end of the balloon.

6. The elastic-balloon-type tamponade device of claim 1 further comprising one or more cladding elements at or on the exterior surface of the balloon, the cladding elements being configured in such a way that at least a portion of the balloon is contained within a housing formed by the one or more cladding elements when the tamponade device is uninflated.

7. The elastic-balloon-type tamponade device of claim 6 wherein the one or more cladding elements are semi-rigid or rigid.

8. The elastic-balloon-type tamponade device of claim 6 wherein the one or more cladding elements extend along the surface of the balloon from a distal end of the balloon toward the proximal end of the balloon.

9. The elastic-balloon-type tamponade device of claim 6 wherein the suction element and the one or more cladding elements are further configured in such a way that at least a portion of the suction element is also contained within said housing when the tamponade device is uninflated.

10. The elastic-balloon-type tamponade device of claim 9 wherein the suction element is comprised of a central region and one or more arms extending along the surface of the tamponade device in between respective pairs of the cladding elements.

11. The elastic-balloon-type tamponade device of claim 1 further comprising at least one of a) at least one valve connected to the inflation portal and b) at least one valve connected to the suction portal.

* * * * *